(12) United States Patent
Rapp

(10) Patent No.: US 7,887,588 B2
(45) Date of Patent: Feb. 15, 2011

(54) INTERBODY SPINAL FUSION DEVICE

(76) Inventor: Lawrence G. Rapp, 7650 Dixie Hwy., #140, Clarkston, MI (US) 48346

( * ) Notice: Subject to any disclaimer, the term of this patent is extended or adjusted under 35 U.S.C. 154(b) by 66 days.

(21) Appl. No.: 11/643,005

(22) Filed: Dec. 19, 2006

(65) Prior Publication Data

US 2007/0276375 A1    Nov. 29, 2007

Related U.S. Application Data

(63) Continuation of application No. 10/475,456, filed as application No. PCT/US02/10699 on Apr. 4, 2002, now abandoned.

(60) Provisional application No. 60/381,579, filed on Apr. 4, 2001.

(51) Int. Cl.
*A61F 2/44* (2006.01)
(52) U.S. Cl. .................................. 623/17.11
(58) Field of Classification Search ... 623/17.11–17.16; 606/90, 247–249
See application file for complete search history.

(56) References Cited

U.S. PATENT DOCUMENTS

| | | | | |
|---|---|---|---|---|
| 4,599,086 A | * | 7/1986 | Doty | ......................... 606/86 A |
| 4,892,545 A | * | 1/1990 | Day et al. | ................. 623/17.11 |
| 4,961,740 A | | 10/1990 | Ray et al. | |
| 5,015,247 A | | 5/1991 | Michelson | |
| 5,470,333 A | | 11/1995 | Ray | |
| 5,484,437 A | | 1/1996 | Michelson | |
| 5,489,308 A | | 2/1996 | Kuslich | |
| 5,522,899 A | | 6/1996 | Michelson | |
| 5,888,223 A | | 3/1999 | Bray | |
| 5,902,304 A | | 5/1999 | Walker et al. | |
| 5,916,267 A | * | 6/1999 | Tienboon | .................. 623/17.11 |
| 5,947,971 A | | 9/1999 | Kuslich et al. | |
| 6,007,536 A | | 12/1999 | Vue | |
| 6,045,579 A | | 4/2000 | Hochshuler | |
| 6,066,175 A | * | 5/2000 | Henderson et al. | ........ 623/17.11 |
| 6,102,950 A | * | 8/2000 | Vaccaro | .................... 623/17.16 |
| 6,106,557 A | * | 8/2000 | Robioneck et al. | ........ 623/17.15 |
| 6,113,638 A | | 9/2000 | Williams et al. | |
| 6,146,421 A | * | 11/2000 | Gordon et al. | ........... 623/17.15 |

(Continued)

FOREIGN PATENT DOCUMENTS

FR    2805457    8/2001

(Continued)

*Primary Examiner*—Eduardo C Robert
*Assistant Examiner*—Mary Hoffman
(74) *Attorney, Agent, or Firm*—Rohm & Monsanto, PLC

(57) ABSTRACT

A pair of flat support plates in a spinal fusion implant device contact and rest against the softer, central cancellous bone portion of respective endplates of adjacent vertebrae. Each support plate has a front template that is orthogonal to the plate and is bent to communicate with the anterior surface of the hard cortical endplate the vertebrae. A wedge-shaped support strut in a central channel between the two plates is configured to vary the distance between the support plates such that the height of the device proximate the anterior end is greater than the height of the device at the posterior end to maintain the natural lordosis of the spine. Channels formed on either side of the support strut are filled with bone graft material and contact the endplates of the vertebrae through large openings in the flat support plates to facilitate fusion.

11 Claims, 2 Drawing Sheets

U.S. PATENT DOCUMENTS

| | | |
|---|---|---|
| 6,190,414 B1 | 2/2001 | Young |
| 6,277,149 B1 | 8/2001 | Boyle et al. |
| 6,302,914 B1 | 10/2001 | Michelson |
| 6,342,074 B1 | 1/2002 | Simpson |
| 6,395,030 B1 * | 5/2002 | Songer et al. ............ 623/17.11 |
| 6,432,106 B1 * | 8/2002 | Fraser .................... 623/17.11 |
| 6,752,808 B2 | 6/2004 | Schumacher |
| 6,786,910 B2 | 9/2004 | Cohen et al. |
| 7,214,243 B2 * | 5/2007 | Taylor .................... 623/17.11 |

FOREIGN PATENT DOCUMENTS

| | | |
|---|---|---|
| WO | WO00-012033 | 3/2000 |
| WO | WO0162190 A1 | 8/2001 |

* cited by examiner

INTERBODY SPINAL FUSION DEVICE

RELATIONSHIP TO OTHER PATENT APPLICATION

This application is a continuation of U.S. Ser. No. 10/475,456 filed on Mar. 8, 2004 now abandoned, which is a United States national stage filing under 35 U.S.C. §371 of international application number PCT/US2002/10699 filed on Apr. 4, 2002, and claims the benefit of U.S. Provisional Patent Application No. 60/381,579, filed Apr. 4, 2001.

BACKGROUND OF THE INVENTION

1. Field of the Invention

This invention relates generally to a spinal implant system, and more particularly, to an interbody spinal fusion device for promoting the fusion of two adjacent vertebrae.

2. Description of the Related Art

There is a need in the field of neurosurgery to have spinal implant systems that allow surgeons to increase the probability of successful vertebral fusion procedures. Intervertebral discs that become degenerated due to various factors such as trauma, aging, or disease may be partially or fully removed as a method of pain control. In a process that is referred to as "interbody fusion," bone graft material is placed into the intervertebral space where the disc was removed to enable adjacent vertebrae to grow together and become one solid piece of bone.

Fusion may require weeks, sometimes months, to achieve a desirable result. If relative movement takes place between the adjacent vertebrae while fusion is underway there is a risk of unsatisfactory results, and at a minimum, the rate of fusion will be retarded. Relative movement may also cause back pain after surgery. In addition, it is necessary to support the spine during fusion in order to maintain the height of the spine (i.e, intervertebral spacing) and, preferably also to maintain the normal lordosis of the spine.

Therefore, once the intervertebral disc is removed, an implant device is typically inserted between neighboring vertebrae to maintain normal disc spacing and restore spinal stability while facilitating intervertebral fusion.

Known implant devices for facilitating fusion include a threaded spinal implant comprising a hollow externally-threaded cylinder into which bone chips or slurry is placed. The cylinder is inserted into the intervertebral space and has holes extending radially therethrough so that bone material grows though the holes to fuse with the bone material of the vertebrae. Illustrative devices of this type are described in U.S. Pat. Nos. 5,947,971; 5,522,899; 5,489,308; 5,015,247; and 4,961,740. Commercial devices of this type include the Sulzer Spine-Tech, Inc. BAK™ surgical implant.

One problem with the implant devices of the type mentioned above is that they tend not to maintain the normal lordosis of the spine. In a healthy state, the cervical and lumbar areas of the human spine are lordotic such that they curve convexly forward. Normal lordosis results, at least in significant measure, from the normal wedge-shaped nature of the spaces between adjacent pairs of the cervical and lumbar vertebrae, and the normal wedge-shaped nature of the intervertebral discs that fill these spaces. Loss of lordosis and proper intervertebral spacing may result in an increased risk of degeneration to other intervertebral discs located adjacent to the fusion level due to the alteration of the overall mechanics of the spine. There is, therefore, a need for an interbody spinal fusion device that maintains normal disc spacing and lordosis.

As a result of the need to maintain proper intervertebral spacing, in this known arrangement, it is necessary to have multiple implant devices, in varying sizes, available for any given operation. For example, the Sulzer Spine-Tech, Inc. BAK™ system includes four different sizes of threaded implants as well as multiple varieties of other implements. This, of course, greatly increases the cost of the implant.

A further problem with the implant mentioned above is that the cylindrical geometry of the engaging element tends to provide a small area of contact between the engaging element and the vertebrae. The small engaging surface tends to contribute to subsidence or deformation of the cortical layer of the vertebrae adjacent to the engaging element. Moreover, the small engaging surface provides less contact between the bone graft material encased in the device and the adjacent vertebrae. Exposure of the bone graft material to the surface of the vertebrae is important because the more exposure, the greater the possibility of having fusion occur. There is, therefore, a need for an interbody spinal fusion device that permits an increased area of exposure of bone graft material to the adjacent vertebrae.

In addition to the foregoing, placement of the known devices is difficult and can shift as a result of procedures during the operation and after the operation. Further, despite the tendency of the threaded exterior to grip the endplates of adjacent vertebrae, the generally cylindrical character of these implant devices can permit relative movement of the vertebrae to take place.

Another type of known implant device is a cage element that has two engaging plates that fit into the intervertebral region. The height between the two plates is then adjusted by some mechanism so that the top plate rests firmly against the upper vertebrae and the lower engaging plate rests firmly against the lower vertebrae. Bone graft material is then inserted in to the cage element. The top and bottom engaging plates have holes that allow the bone graft material to come in contact with the vertebral surface. The cage element differs from the externally-threaded cylinder implant discussed above because the cage element has more surface area that is in contact with the adjacent vertebrae. However, the holes in the top and bottom plates are the only exposure that the bone graft material has to the vertebral surface. In this regard, the cage element is not significantly better that the externally-threaded cylinder implant.

Further, the cage element rests against the softer cancellous bone in the center of the vertebral bodies and/or is provided with protrusions or teeth to facilitate engagement with the cancellous bone tissue. The cage element is, therefore, not attached to the harder, outer ring of cortical bone. Moreover, engagement of the device to the cancellous bone surface causes damage that can result in subsidence.

There is, therefore, a need in the art for an interbody spinal fusion device that decreases the risk of subsidence and provides a larger area of contact between bone graft material and adjacent vertebrae. There is also a need in the art for an interbody spinal fusion device that maintains normal lordosis.

SUMMARY OF THE INVENTION

The foregoing and other objects are achieved by the present invention which provides an interbody spinal fusion device that facilitates bone fusion between adjacent vertebrae of a human spine. In accordance with the invention, the interbody spinal fusion device is provided with a pair of bone-engaging plate members that are adapted to engage respective ones of the vertebrae. The bone-engaging plate members are, once installed, accommodated between the adjacent vertebrae, and as will be described herein, facilitate maintenance of the respective vertebrae in a predetermined spaced apart relationship. The interbody fusion device having an anterior end distal from a posterior end. Each of the bone-engaging plate members is provided with an associated support plate that is configured to communicate intimately with an endplate of an associated one of the adjacent vertebrae. The support plates each have an outer surface that contacts the associated vertebra and an inner surface that is directed toward the other of the adjacent vertebrae. In addition, the support plates have apertures therethrough and at least one longitudinal support plate portion extending substantially through the support plate from the anterior end thereof to the posterior end thereof. There is additionally provided a generally curved template having a first template surface extending outward substantially orthogonal with respect to the horizontal plane of the support plate in the direction of the outer surface of the support plate. The first template surface faces in the posterior direction and is arranged for communicating with a substantially lateral anterior cortical surface portion of the associated vertebra. In addition, the template has an anterior surface. A support strut is interposed between the respective inner surfaces of the bone-engaging plate members, the support strut being arranged to extend substantially parallel to the longitudinal support plate portion. The support strut is adapted to maintain the bone-engaging plate members apart in a predetermined spatial relationship wherein a distance between the respective inner surfaces proximate the anterior end is greater that the distance proximate the posterior end. In this manner, a substantially natural lordosis of the human spine is maintained.

In one embodiment of the invention, the support plate is configured to be generally flat. However, in other embodiments the support plate is adapted to follow the generally contour of the endplate of the vertebra with which it communicates. In the specific illustrative embodiment of the invention, the support plate is provided with three longitudinal members that define two large apertures through the support plate. The longitudinal members terminate in a generally curved section at the posterior end, and terminate with the template at the anterior end.

In a further embodiment of the invention, the anterior surface of at least one template is provided with at least three apertures for accommodating fasteners. Such apertures preferably are configured to determine the angle of penetration of the fasteners into each vertebra, and may, in certain embodiments, be orthopedic bone screws.

In a particularly advantageous embodiment, the support plate includes at least two tabs that are integrally formed, and coplanar, with the anterior surface of the template. These tabs extend in the direction of the inner surface of the support plate. Two adjacent tabs guide the support strut, which may have a wedge shape, between the bone-engaging plate members during placement. More specifically, the two adjacent tabs define an opening into the region between the adjacent vertebrae that has a width approximately equal to the width of the support strut.

At least one of the support plates includes a protuberance on the inner surface of the longitudinal member proximate the posterior end to preclude over-insertion of the support strut in the posterior direction.

Bone graft material is packed into channels that are formed on either side of the support strut and that extend between the support plates. The bone graft material communicates with the vertebrae through the openings in the support plates.

In a still further embodiment, there is additionally provided an end cap proximate the anterior end. The end cap may, in certain embodiment, be coupled to the anterior surfaces of the curved templates of the bone-engaging plate members.

BRIEF DESCRIPTION OF THE DRAWING

Comprehension of the invention is facilitated by reading the following detailed description, in conjunction with the annexed drawing, in which.

DETAILED DESCRIPTION

Figure 1:
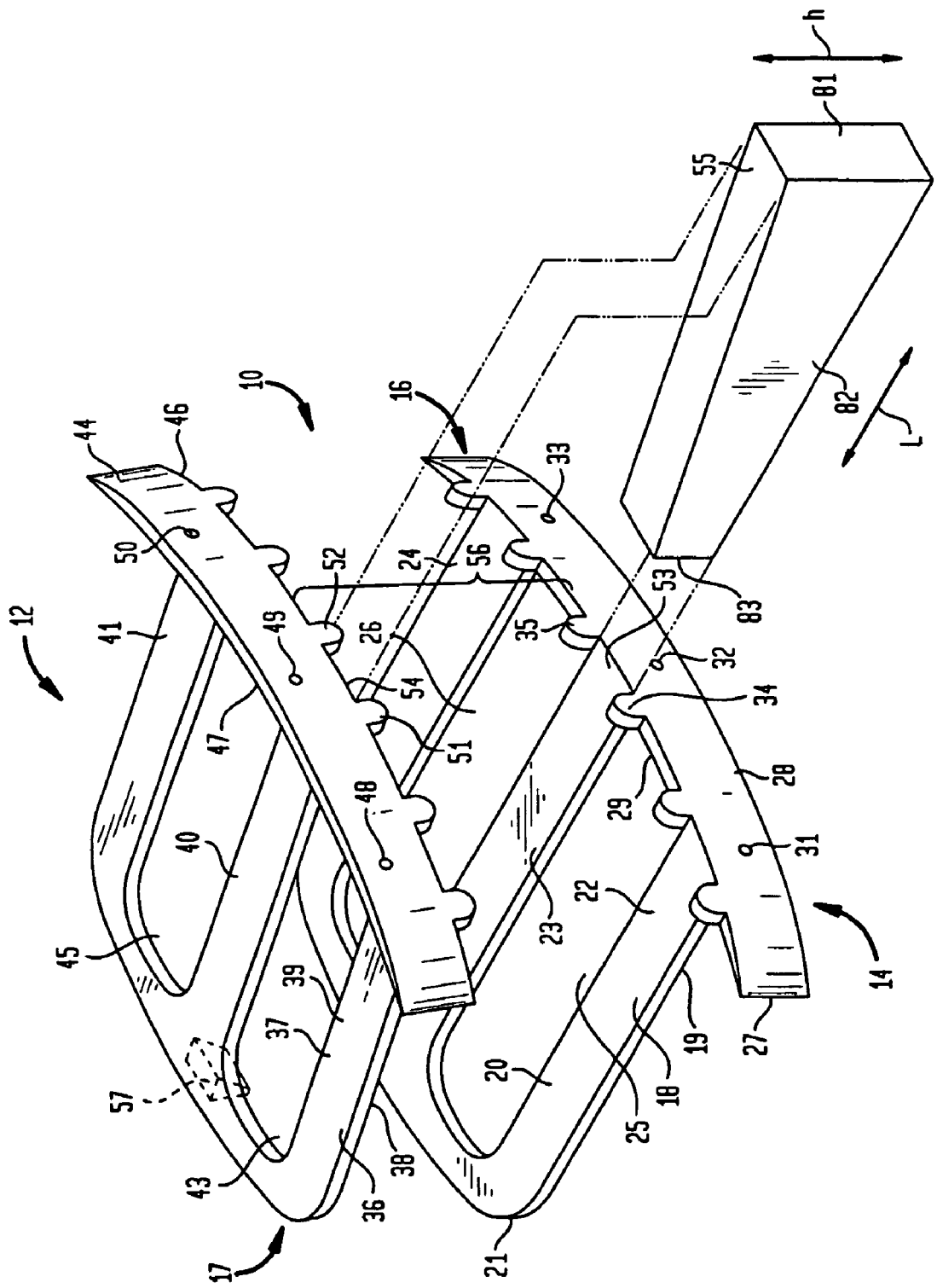
FIG. 1 is a perspective view of an interbody spinal fusion device in accordance with the invention.

FIG. 1 is a perspective view of the interbody spinal fusion device 10. Interbody spinal fusion device 10, suitable for implantation in the intervertebral space between two adjacent vertebral bodies (not shown), has a pair of bone-engaging plate members, specifically top plate member 12 and bottom plate member 14. In use, top plate member 12 and bottom plate member 14 are arranged above and below each other, respectively, in spaced apart relationship. The spaced apart relationship is created and maintained in a manner that will be described more completely hereinbelow.

Bottom plate member 14 has a bottom support plate 18 that is adapted to rest on the endplate of the lower vertebra (not shown). Bottom support plate 18 has an outer surface 19 that contacts the lower vertebra and an inner surface 20. As shown in this figure, bottom support plate 18 is generally flat, but may be adapted to follow the contour of the vertebra on which it rests. Since the support plates merely contacts the endplates of the vertebrae, and can be bent to the contour of the vertebrae, rather than engage by means of protuberances or engaging teeth, there is less damage to the bone which prevents subsidence. In this embodiment, bottom support plate 18 has three longitudinal support plate portions, or longitudinal members 22, 23, and 24 that terminate in a generally curved section 21 at posterior end 17. Longitudinal members 22, 23, and 24 define two large openings 25 and 26.

At anterior end 16, longitudinal members 22, 23, and 24 terminate with a generally curved section that is bent substantially orthogonal to the horizontal plane of bottom support plate 18 in the direction of communication of the template and the vertebral body. The generally curved section is herein referred to as bottom template 27. Bottom template 27 has an anterior front face surface 28 at anterior side 16 of the device and an opposing posterior surface 29 (designated, but not specifically shown in this figure). Posterior surface 29 is adapted to contact and rest flush against the curved anterior cortical surface of the lower vertebra (not shown).

In this embodiment, bottom template 27 is provided with three pre-drilled holes 31, 32 and 33 which may, in some embodiments, be internally threaded. Fasteners, such as threaded orthopedic bone screws (not shown) are inserted through the pre-drilled holes and into the hard cortical bone of the anterior surface of the vertebra. In preferred embodiments, the pre-drilled holes may be configured to adjust the angle of placement of the bone screws so that the bone screws can be set to work against each other in order to stabilize the device.

While a total of six bone screws are used in the specific embodiment described herein, it is to be understood that the bone-engaging plate members can be attached to vertebrae using a greater or lesser number of fasteners depending on different variables, including, but certainly not limited to, size or bone density of the vertebrae, spatial positioning of the vertebrae, and the level of attachment required by the physician.

Orthopedic bone screws of the type suggested for use in the practice of the invention are well-known and available from a variety of suppliers known to those of ordinary skill in the art. However, it is to be understood, that other known or new and improved forms of orthopedic screws and other types of improved orthopedic fasteners and fastening systems are within the contemplated scope of the invention.

Top plate member 12 is generally equivalent in structure to bottom plate member 14, and in some embodiments, may be identical in structure to bottom plate member. However, in use, the top plate member 12 is flipped so that top template 44 will be bent substantially orthogonal to the horizontal plane of top support plate 36 in the direction of communication of the template and the vertebral body.

Referring to FIG. 1, top plate member 12 has a top support plate 36 that is adapted to rest on the endplate of the upper vertebra (not shown). Top support plate 36 has an outer surface 37 that contacts the upper vertebra and an inner surface 38 (designated, but not specifically shown in this figure). Top support plate 36 has three longitudinal members 39, 40, and 41 that terminate in a generally curved section 42 at posterior end 17. Longitudinal members 39, 40 and 41 define two large openings 43 an 45. At anterior end 16, longitudinal members 39, 40 and 41 terminate with top template 44. Top template 44 has an anterior front face surface 46 at anterior side 16 of the device and an opposing posterior surface 47 (designated, but not specifically shown). Posterior surface 47 is adapted to contact and rest flush against the curved anterior cortical surface of the upper vertebra (not shown). Top template 44 is also provided with three pre-drilled holes 48, 49, 50.

Bottom template 27 has tabs, illustratively adjacent tabs 34 and 35, that are integrally formed, and coplanar with, the anterior front face of bottom template 27, but extend in a direction opposite to the direction that the template is bent. For bottom template 27, the tabs extend upward from its inner surface 20. Tabs 34 and 35 form an initial guide, or slot 53, that precludes transverse dislocation of support strut 55 when inserted into the interbody spinal fusion device. In this specific embodiment, the tabs are spaced apart to define an opening having a width approximately equal to the width of central longitudinal member 23. Top template 44 also has tabs, illustratively tabs 51 and 52, that define a slot 54. However, in the case of top template 44, the tabs extend in a direction downward from its inner surface 38. When top plate member 12 and bottom plate member 14 are mounted to adjacent vertebrae, as will be described hereinbelow, tabs 34 and 35 in combination with tabs 51 and 52, are aligned to form generally an aperture 56 into which wedge-shaped support strut 55 is inserted.

In addition to the foregoing, in some embodiments additional tabs (shown, but not specifically designated, in FIG. 1) may be provided. In these embodiments, the tabs can operate to define additional slots/apertures for the insertion of more than one support strut. The tabs, which extend in an opposing direction to the main body of the template, and in front of the channels into which bone graft material will be placed, can also operate to stabilize and anchor the device.

The interbody spinal fusion device 10 has a height that is defined by the vertical distance between the outer surface 39 of top support plate 36 and the outer surface 19 of bottom support plate 18. The height is adjustable by selection and insertion of a strut of the appropriate size into aperture 56, and preferably, varies along the interbody spinal fusion device 10 between anterior end 16 and posterior end 17 so as to maintain the natural lordosis of the spine.

Referring to exemplary strut 55, shown in FIG. 1 prior to insertion, support strut 55 comprises a solid wedge-shaped object of a predetermined maximum height at anterior end 81 and minimum height at posterior end 83. The angle of the wedge-shaped strut is determined by the height of posterior end 83 relative to the height of anterior end 81. In a kit embodiment of the invention, a selection of support struts of varying height and/or angle would be provided along with the top and bottom plate members in a surgical kit so that the practitioner can select the appropriate strut for the individual patient. The angle of support strut 55 is chosen to maintain the lordosis of the vertebral column. The height of support strut 55 is chosen to approximate the height of the disc material that previously occupied the intervertebral spacing. It is anticipated that as few as two or three support struts will be all that is required to practice the invention. Of course, this number is illustrative and is in no way intended to be limiting. This is a significant reduction in the amount of parts required for a surgical kit for an interbody fusion operation.

In use, support strut 55 is inserted in aperture 56 between longitudinal members 23 and 40, spanning the intervertebral region and resting firmly against the upper and lower vertebrae. In some embodiments, top plate 36 has a protrusion 57 to engage support strut 55 to prevent over-insertion. Of course, either one or both the bottom plate 18 or top plate 36 can be provided with a protrusion for this purpose.

Figure 2:
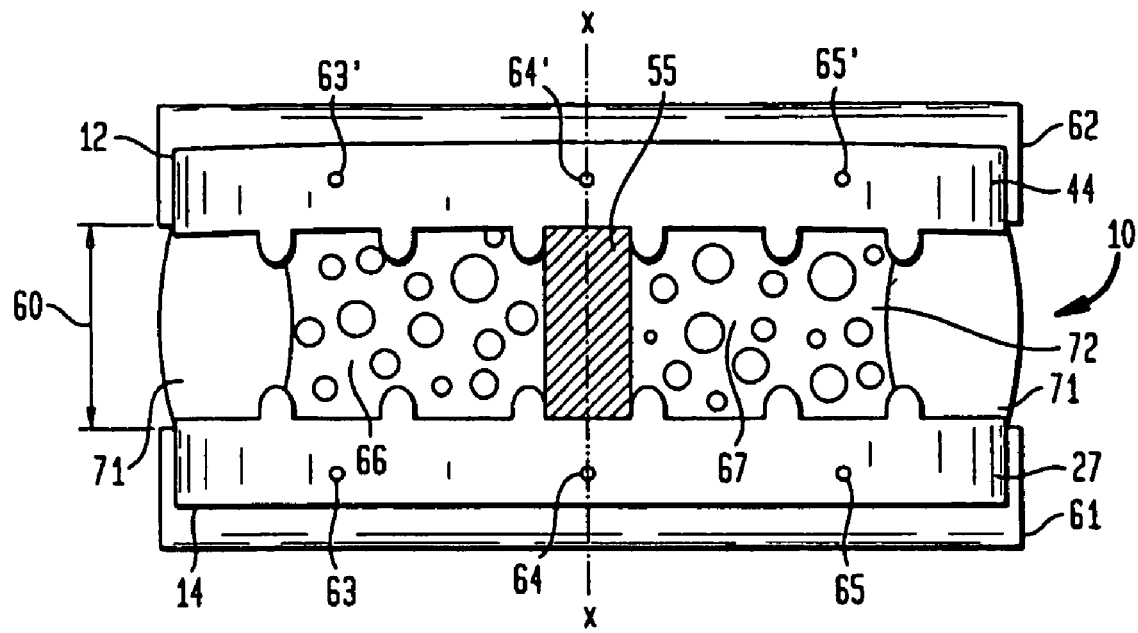
FIG. 2 is a plan view, from the anterior side, of a portion of the spinal column with the interbody spinal fusion device of FIG. 1 mounted between two adjacent vertebrae.

FIG. 2 is a plan view of a portion of the spinal column with interbody fusion device 10 mounted between two vertebrae. Elements of structure that are identical to those in FIG. 1 are similarly designated in FIG. 2. Interbody spinal fusion device 10 is placed in intervertebral region 60 between a first vertebra 61 located below intervertebral region 60 and a second vertebra 62 located above intervertebral region 60. Bottom plate member 14 is attached to vertebra 61 by bone screws 63, 64, and 65 that are inserted through pre-drilled holes (see FIG. 1) in bottom template 27. Top plate member 12 is attached to vertebra 62 by bones screws 63', 64', and 65' through top template 44. Support strut 55 is shown inserted in aperture 56.

Channels 66 and 67 are formed on either side of support strut 55 for packing bone graft material 72 to facilitate fusion of vertebra 61 with vertebra 62. Referring to FIG. 1, openings 25 and 26 in bottom support plate 18 (not shown in this figure) and openings 43 and 45 in top support plate 36 (not shown in this figure) underlie or overlie, respectively, channels 66 and 67 so that there is a large area of contact of bone graft material with the vertebrae.

In some embodiments, an end cap (not shown in this figure) is placed over the top and bottom templates to lock the support strut in place. Advantageously, the end cap will assist in retaining bone graft material in the channels. Preferably, the outermost portions of the lateral and posterior annulus 71 remain intact and serve to confine the bone graft material in lateral and posterior directions. Of course, a retaining plate (not shown) for the posterior side of spinal fusion device 10 can be devised, by persons of skill in the art, for retaining bone graft material, if required.

The components of the interbody spinal fusion device of the present invention are constructed of biocompatible materials, and presently titanium or titanium alloys are preferred. However, it is to be understood that other materials presently known, and to be developed, that have the appropriate strength and biocompatibility, such as ceramics, metals, and carbon composites, are specifically contemplated for use in connection with the invention.

In practice, the interbody spinal fusion device of the present invention is installed in accordance with techniques known to those of ordinary skill in the art. Illustratively, the technique utilizes an anterior approach to the spine and is particularly suited to fusion of lumbar or thoracic vertebrae. The annulus of the affected disc is sharply incised anteriorly to allow a complete discectomy to be performed. Preferably, the entire disc is removed except for the outermost portions of the lateral and posterior annulus. The endplates of the vertebrae are carefully scraped clean of all disc material.

Figure 3:
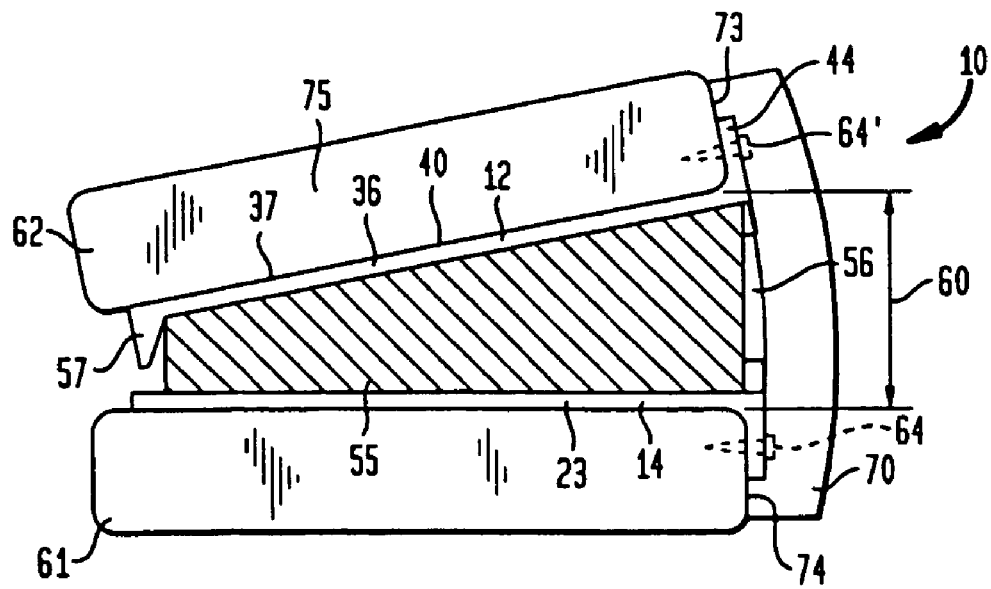
FIG. 3 is a cross-sectional side view of the mounted interbody spinal fusion device of FIG. 2, taken along line X-X.

The top plate member 12 and the bottom plate member 14 are respectively placed into the intervertebral space, as shown in FIG. 3, which is a cross-sectional side view of spinal fusion device 10, taken along line X-X in FIG. 2, as installed between neighboring vertebrae 61 and 62. Elements of structure that are identical to those in FIG. 1 or FIG. 2 are similarly designated in FIG. 3.

Referring to FIG. 3, by way of illustration, top plate member 12 is mounted into intervertebral region 60 by placing template 44 on the anterior surface 73 of the hard cortical endplate of the upper vertebra 62. This results in the insertion of support plate 36 into intervertebral region so that its outer surface 37 contacts the cleaned, softer center of cancellous bone 75 where the disc has been removed (designated, but not specifically shown). Template 44 is shown attached to the hard cortical bone by surgical screw 64'. Bottom plate member 14 is mounted into intervertebral region 60 and attached to vertebra 61 in a similar manner by fastening bottom template 27 on the anterior surface 74 of the hard cortical endplate of the lower vertebra 61.

The height and width of the disc space are measured, and a support strut 55 having the correct height and/or angle to restore and maintain the appropriate intervertebral spacing and normal spinal lordosis is selected by the surgeon. Support strut 55 is then inserted into aperture 56 created by center slots 54 and 53 (see FIG. 1) and will rest between central longitudinal members 23 and 40. Protuberance 57 on central longitudinal member 40 will act as a stop to prevent over-insertion of support strut 55.

Once the desired height and angle is achieved, bone graft material (not shown in this figure) is packed into hollow channels (shown as channels 66 and 67 in FIG. 2) on either side of support strut 55. The remaining outermost portions of the lateral and posterior annulus (not shown in this figure) may serve to retain the packed bone graft material in place. In this particular embodiment, removable end plate 70, which may be fastened to template members 44 and 27 by force-fit or fasteners, locks spinal fusion device 10 in place and retains bone graft material in the anterior direction.

Known techniques, such as x-ray imaging or fluoroscopy, can be used to confirm correct placement of the device and selection of size/angle of the support strut. However, in the practice of the invention, the radius of curvature of the anterior vertebral body would dictate the placement of the template. The depth of the support plate, along with the curvature as it relates to the anterior vertebral body, creates a device that is self-directing as to location. There is no chance of over-penetration of the device inasmuch as depth is limited by the anterior aspect of the vertebral approach. This prevents errors in placement of the type that routinely occur with the known cylindrical threaded fusion devices, such as placement which is too far lateral and, theoretically, can go beyond the cortical margin into the area of the foramen. It also removes the risk of over-drilling that can happen when a cylindrical threaded fusion device is started too far laterally on the vertebral body.

Moreover, it prevents the all-too-frequent complications resulting when the known device does not obtain equal purchase in each endplate.

The interbody spinal fusion device of the present invention is, mechanically, a more stable construct than known prior art devices since there is a greater amount of surface area engaged against the anterior aspect of the vertebral body as well as impacting the vertebral body endplate. This allows for more aggressive removal of cartilaginous endplate and bone from the affected area. Moreover, the interbody spinal fusion device of the present invention provides wide channels into which bone graft material may be packed. In addition, the large openings in the support plate provides for a large area of contact between the bone graft material and the prepared endplates of the vertebrae.

Although the invention has been described in terms of specific embodiments and applications, persons skilled in the art can, in light of this teaching, generate additional embodiments without exceeding the scope or departing from the spirit of the invention described herein. Accordingly, it is to be understood that the drawing and description in this disclosure are proffered to facilitate comprehension of the invention, and should not be construed to limit the scope thereof.

What is claimed is:

1. An interbody spinal fusion device for facilitating fusion between adjacent vertebrae of a human spine, the interbody spinal fusion device comprising:

a pair of bone-engaging plate members adapted to engage respective ones of the vertebrae, and to be accommodated therebetween, for maintaining the respective vertebrae in a predetermined spaced apart relationship, the interbody fusion device having an anterior end distal from a posterior end, the bone-engaging plate members each having;

a support plate configured to communicate intimately with an end plate of an associated one of the adjacent vertebrae, the support plate being substantially planar in a horizontal plane and having an outer surface that is adapted to contact the associated vertebra and an inner surface adapted to be directed toward the other of the adjacent vertebrae, the support plate having apertures therethrough and at least one longitudinal support plate portion extending substantially through the support plate from the anterior end thereof to the posterior end thereof, and a generally curved template disposed at the anterior end of the support plate and having a first template posterior surface extending substantially orthogonal with respect to the horizontal plane of the support plate in the direction of the outer surface of the support plate, the first template posterior surface arranged for communicating with a substantially lateral anterior cortical surface portion of the associated vertebra, the template further having an anterior surface distal to the posterior surface and terminating at the anterior end of the bone-engaging plate member, the template further including at least two tabs that are integrally formed, and coplanar, with the anterior surface of the template, and arranged to extend in the direction of the inner surface of the support plate;

a support strut interposed between the respective inner surfaces of the bone-engaging plate members, said support strut being arranged to extend substantially parallel to the longitudinal support plate portions and to be guided by the tabs, the tabs being spaced apart to define an opening that accommodates the support strut, the support strut being adapted to maintain the bone-engaging plate members apart in a predetermined spatial relationship wherein a distance between the respective inner surfaces proximate the anterior end is greater than the distance proximate the posterior end, whereby a substantially natural lordosis of the human spine is maintained, there being formed channels on either side of said support strut arranged to communicate with the vertebrae via respective ones of the apertures through each of the support plates of the bone-engaging members; and bone graft material packed in the channels, the bone graft material communicating with the vertebrae via the apertures through each of the support plates.

2. The interbody spinal fusion device of claim 1 wherein the support plate is generally flat.

3. The interbody spinal fusion device of claim 1 wherein the support plate is adapted to follow generally the contour of the end plate of the vertebra with which it communicates.

4. The interbody spinal fusion device of claim 1 wherein the support plate comprises three longitudinal support plate portions that define two large apertures through the support plate.

5. The interbody spinal fusion device of claim 4 wherein the longitudinal members terminate in a generally curved section at the posterior end, and terminate with the template at the anterior end.

6. The interbody spinal fusion device of claim 1 wherein at least one template is provided with at least three apertures for accommodating fasteners.

7. The interbody spinal fusion device of claim 6 wherein the apertures are configured to determine the angle of penetration of the fasteners into each vertebra.

8. The interbody spinal fusion device of claim 6 wherein the fasteners are orthopedic bone screws.

9. The interbody spinal fusion device of claim 1 wherein at least one of the support plates includes a protuberance on the an inner surface of the longitudinal support plate portion proximate the posterior end to preclude over-insertion of the support strut in the posterior direction.

10. The interbody spinal fusion device of claim 1 wherein there is further provided an end cap proximate the anterior end.

11. The interbody spinal fusion device of claim 1 wherein the support strut is wedge-shaped.

\* \* \* \* \*